United States Patent
Harlev et al.

(10) Patent No.: US 8,755,861 B2
(45) Date of Patent: *Jun. 17, 2014

(54) CARDIAC MAPPING CATHETER

(71) Applicant: Rhythmia, Medical, Inc., Burlington, MA (US)

(72) Inventors: Doron Harlev, Brookline, MA (US); Justin Callaway, Goffstown, NH (US)

(73) Assignee: Rhythmia Medical, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/868,151

(22) Filed: Apr. 23, 2013

(65) Prior Publication Data

US 2013/0253298 A1   Sep. 26, 2013

Related U.S. Application Data

(63) Continuation of application No. 13/289,367, filed on Nov. 4, 2011, now Pat. No. 8,447,377, which is a continuation of application No. 12/005,975, filed on Dec. 28, 2007, now Pat. No. 8,103,327.

(51) Int. Cl.
*A61B 5/0402* (2006.01)

(52) U.S. Cl.
USPC ............. 600/374; 600/509; 600/393; 29/825

(58) Field of Classification Search
USPC ................ 600/372, 373, 374, 381, 393, 509; 607/122; 606/41
See application file for complete search history.

(56) References Cited

U.S. PATENT DOCUMENTS

| | | |
|---|---|---|
| 4,649,924 A | 3/1987 | Taccardi et al. |
| 4,890,623 A | 1/1990 | Cook et al. |
| 4,940,064 A | 7/1990 | Desai et al. |
| 5,156,151 A | 10/1992 | Imran |
| 5,228,442 A | 7/1993 | Imran |
| 5,255,679 A | 10/1993 | Imran |
| 5,279,299 A | 1/1994 | Imran |
| 5,311,866 A | 5/1994 | Kagan et al. |
| 5,313,943 A | 5/1994 | Houser et al. |
| 5,345,936 A | 9/1994 | Pomeranz et al. |
| 5,415,166 A | 5/1995 | Imran |
| 5,417,982 A | 5/1995 | Modi |
| 5,425,364 A | 6/1995 | Imran |
| 5,456,254 A | 10/1995 | Imran et al. |

(Continued)

FOREIGN PATENT DOCUMENTS

| | | |
|---|---|---|
| WO | 95/13111 | 5/1995 |
| WO | 96/34652 | 11/1996 |

(Continued)

OTHER PUBLICATIONS

Authorized officer Yoshiko Kuwahara, International Preliminary Report on Patentability in PCT/US2008/013553 mailed Jul. 8, 2010, 7 pages.

(Continued)

*Primary Examiner* — Lee S Cohen
*Assistant Examiner* — Erin M Cardinal
(74) *Attorney, Agent, or Firm* — Fish & Richardson P.C.

(57) ABSTRACT

A multi electrode catheter for non contact mapping of the heart having independent articulation and deployment features.

19 Claims, 15 Drawing Sheets

(56) References Cited

U.S. PATENT DOCUMENTS

| | | | |
|---|---|---|---|
| 5,490,859 A * | 2/1996 | Mische et al. | 606/159 |
| 5,647,870 A | 7/1997 | Kordis et al. | |
| 5,681,280 A | 10/1997 | Rusk et al. | |
| 5,681,308 A | 10/1997 | Edwards | |
| 5,697,377 A | 12/1997 | Wittkampf | |
| 5,699,796 A | 12/1997 | Littman et al. | |
| 5,702,438 A | 12/1997 | Avitall | |
| 5,871,443 A | 2/1999 | Edwards et al. | |
| 5,911,739 A * | 6/1999 | Kordis et al. | 607/122 |
| 6,064,905 A | 5/2000 | Webster | |
| 6,690,963 B2 | 2/2004 | Haim | |
| 6,826,421 B1 | 11/2004 | Beatty et al. | |
| 6,837,886 B2 | 1/2005 | Collins et al. | |
| 7,198,635 B2 | 4/2007 | Danek et al. | |
| 7,615,049 B2 | 11/2009 | West et al. | |
| 8,103,327 B2 * | 1/2012 | Harlev et al. | 600/374 |
| 8,224,416 B2 | 7/2012 | de la Rama et al. | |
| 8,447,377 B2 * | 5/2013 | Harlev et al. | 600/374 |
| 2005/0033136 A1 | 2/2005 | Govari et al. | |
| 2005/0033137 A1 | 2/2005 | Oral et al. | |
| 2007/0083194 A1 | 4/2007 | Kunis et al. | |
| 2007/0112342 A1 | 5/2007 | Pearson et al. | |
| 2008/0140152 A1 | 6/2008 | Imran et al. | |
| 2009/0171274 A1 | 7/2009 | Harlev et al. | |
| 2012/0078077 A1 | 3/2012 | Harlev et al. | |

FOREIGN PATENT DOCUMENTS

| | | |
|---|---|---|
| WO | 02/43789 | 6/2002 |
| WO | 2005/114720 | 12/2005 |
| WO | 2006/036408 | 4/2006 |

OTHER PUBLICATIONS

Authorized officer Patricia Jameson, Supplementary Partial European Search Report in Application No. 08867908.9, mailed Sep. 6, 2011, 12 pages.

* cited by examiner

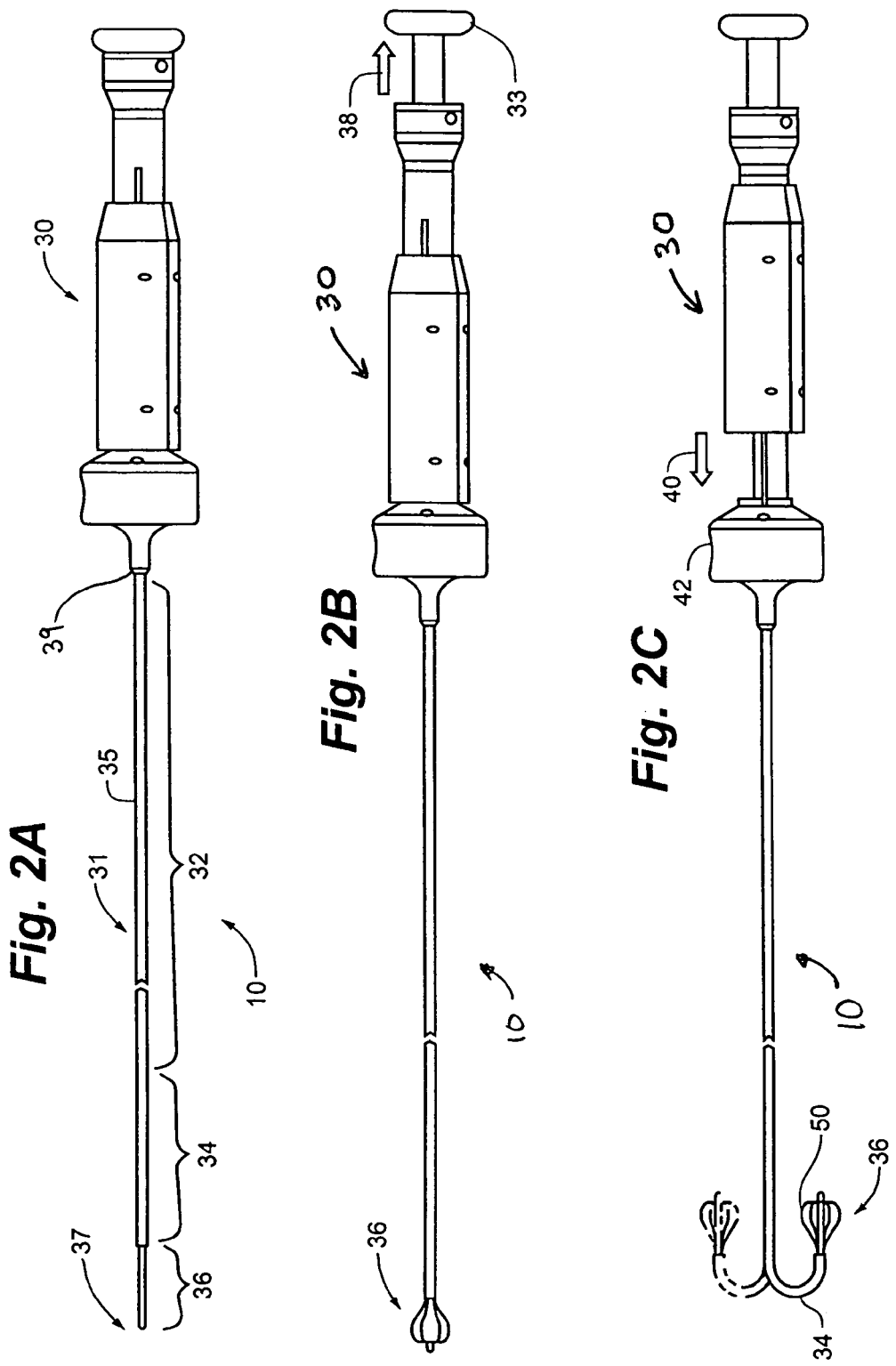

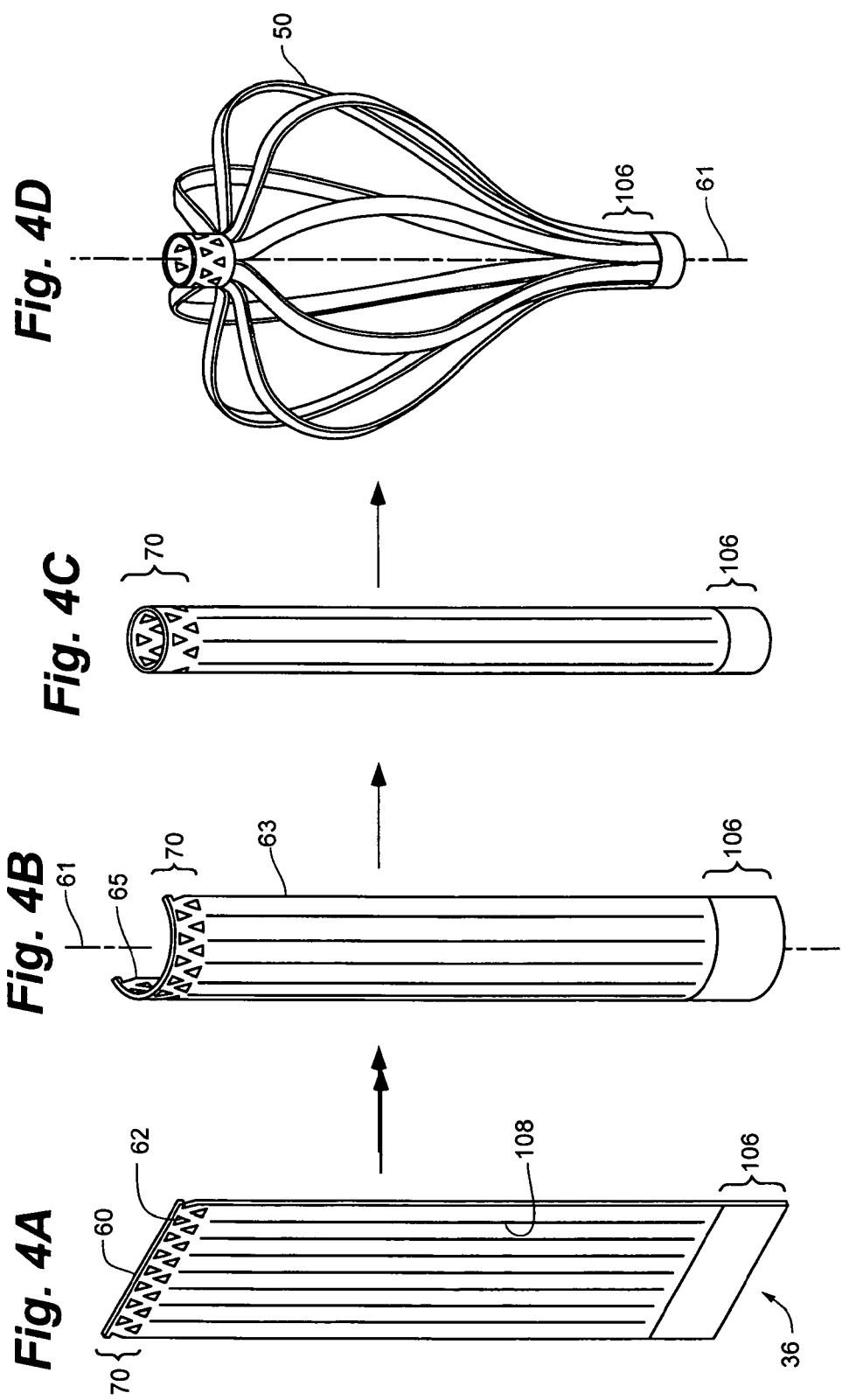

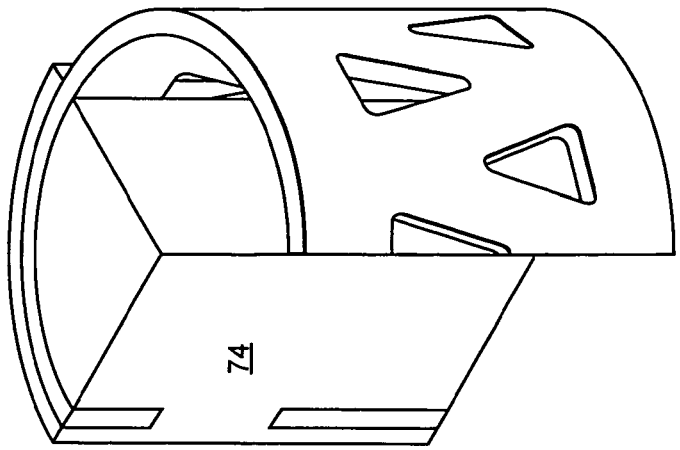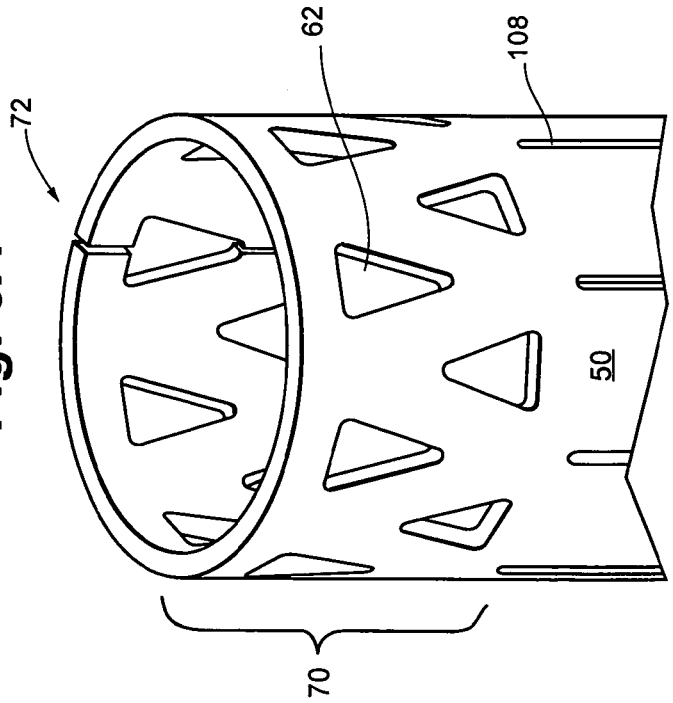

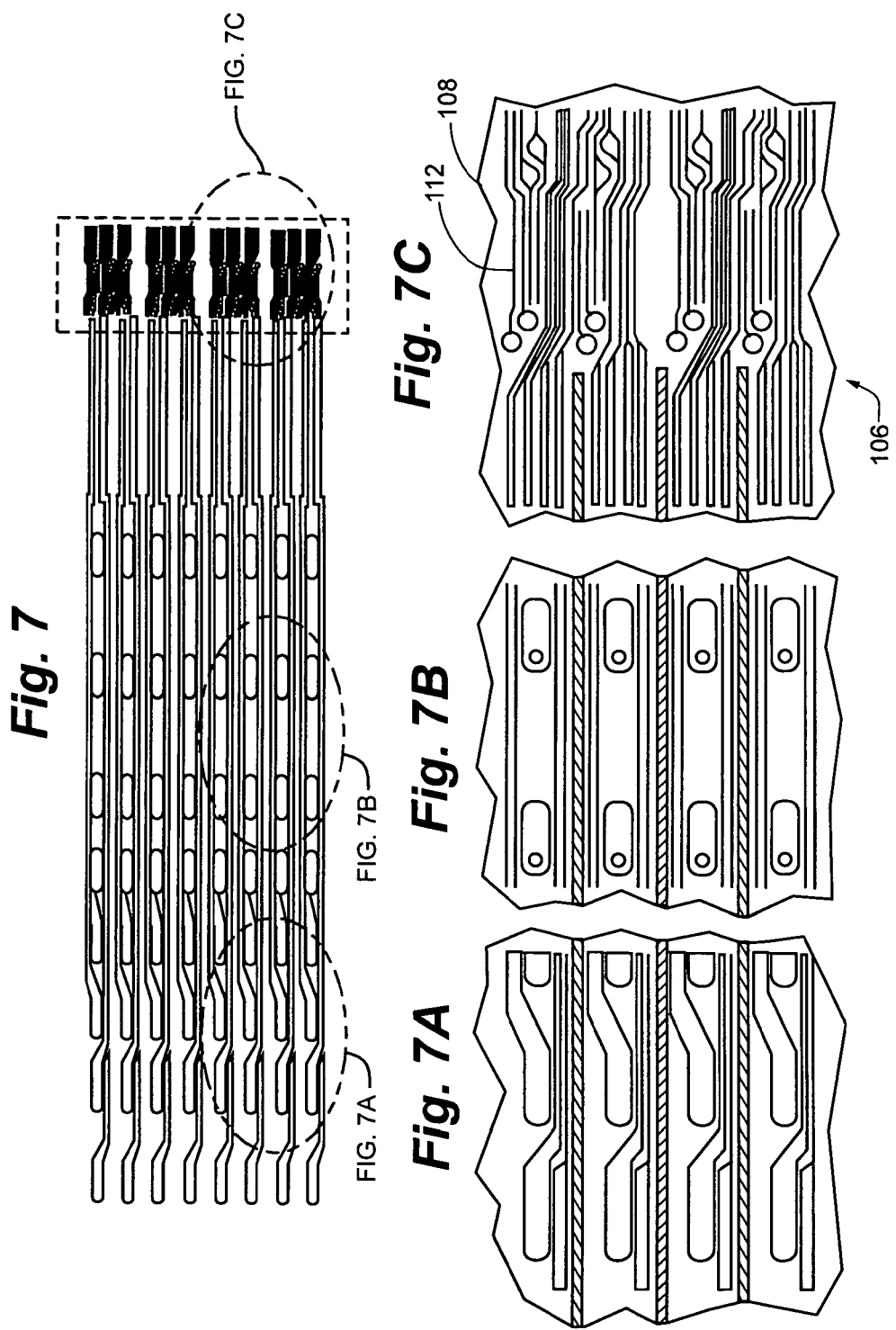

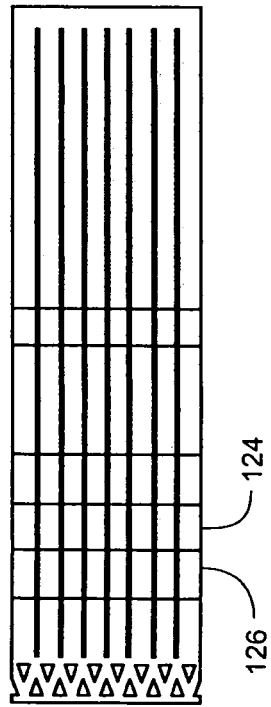
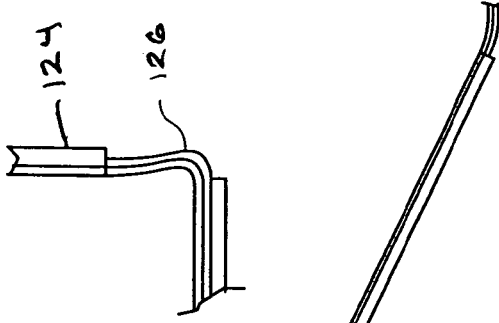
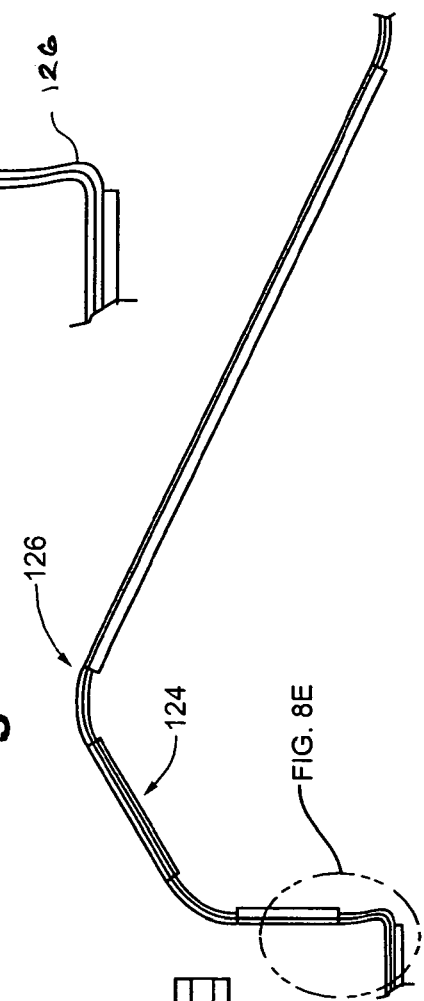
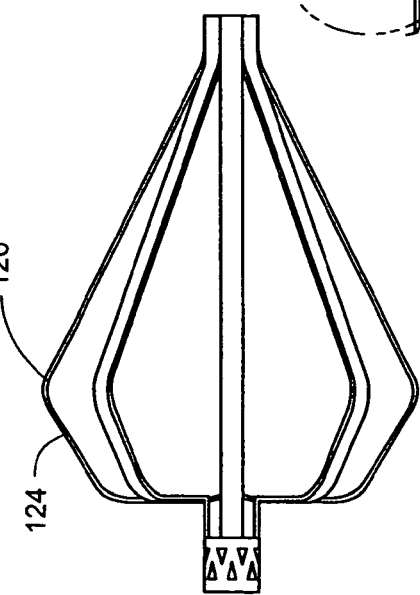

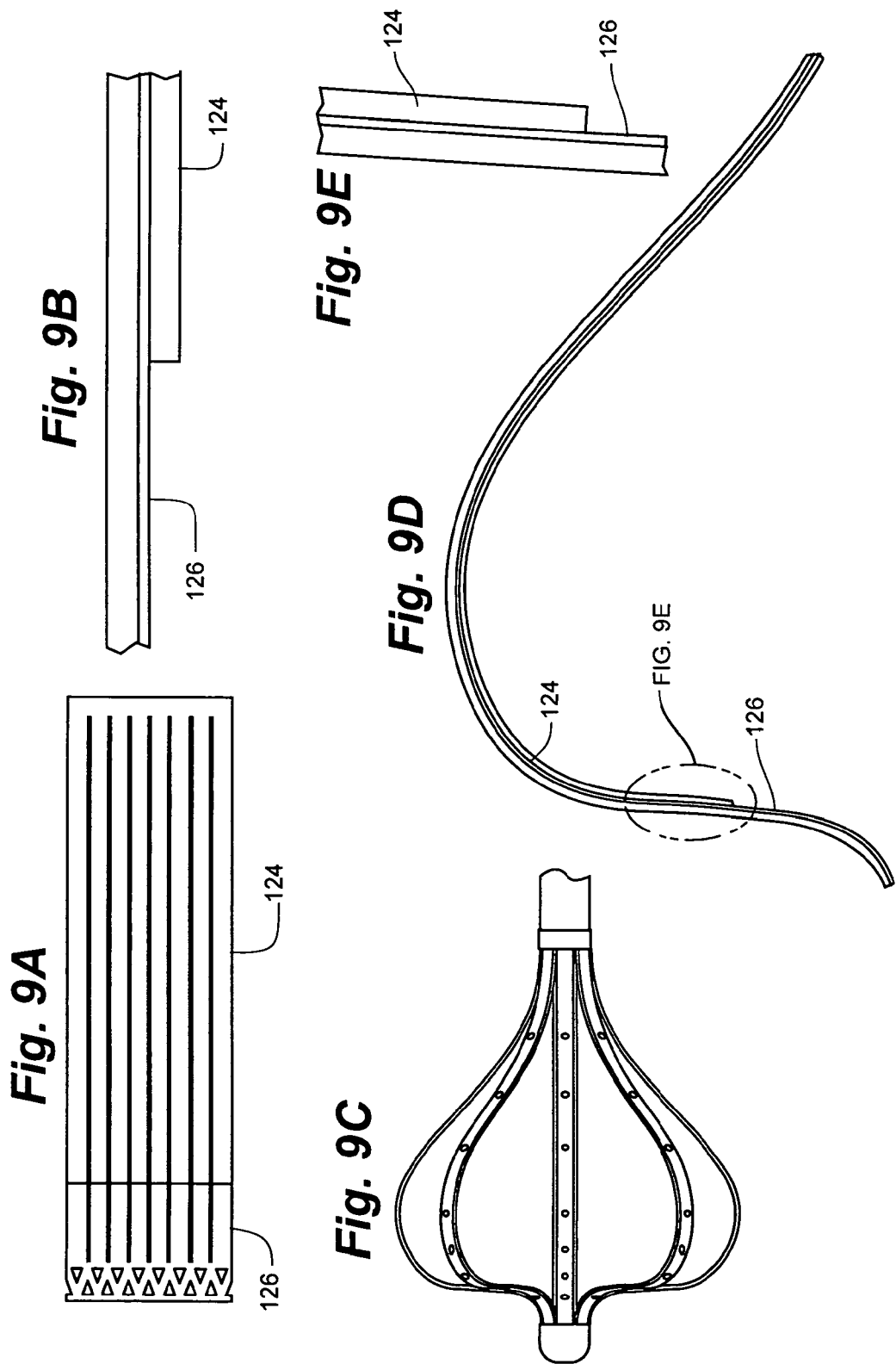

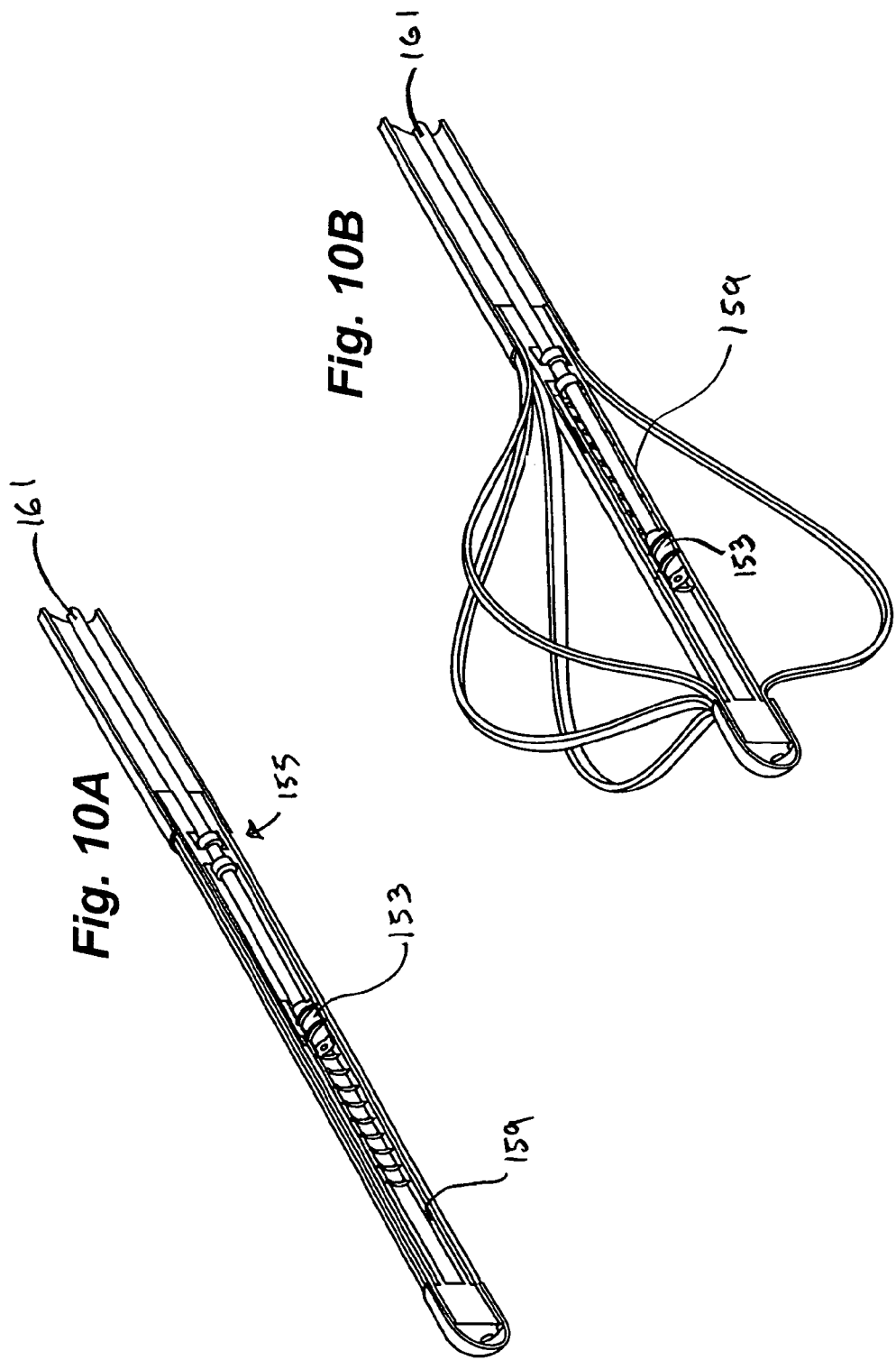

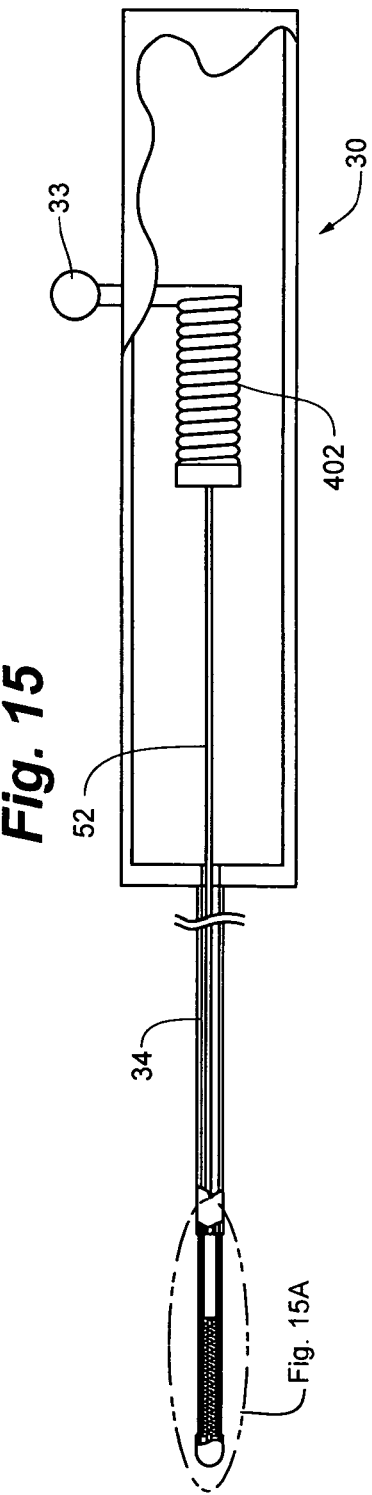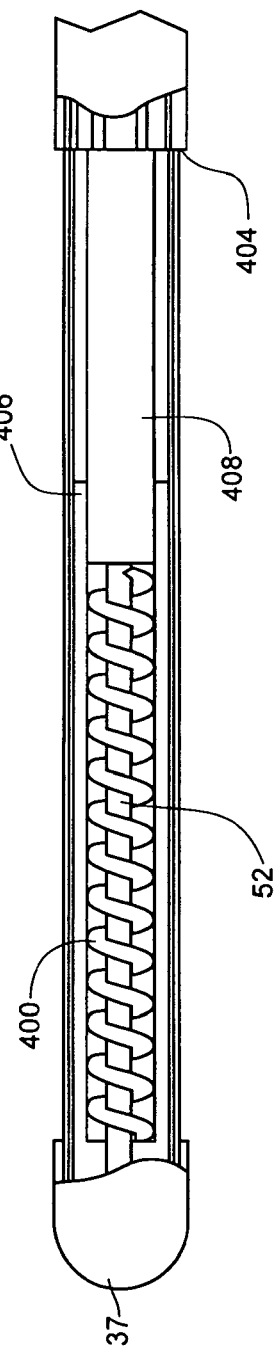

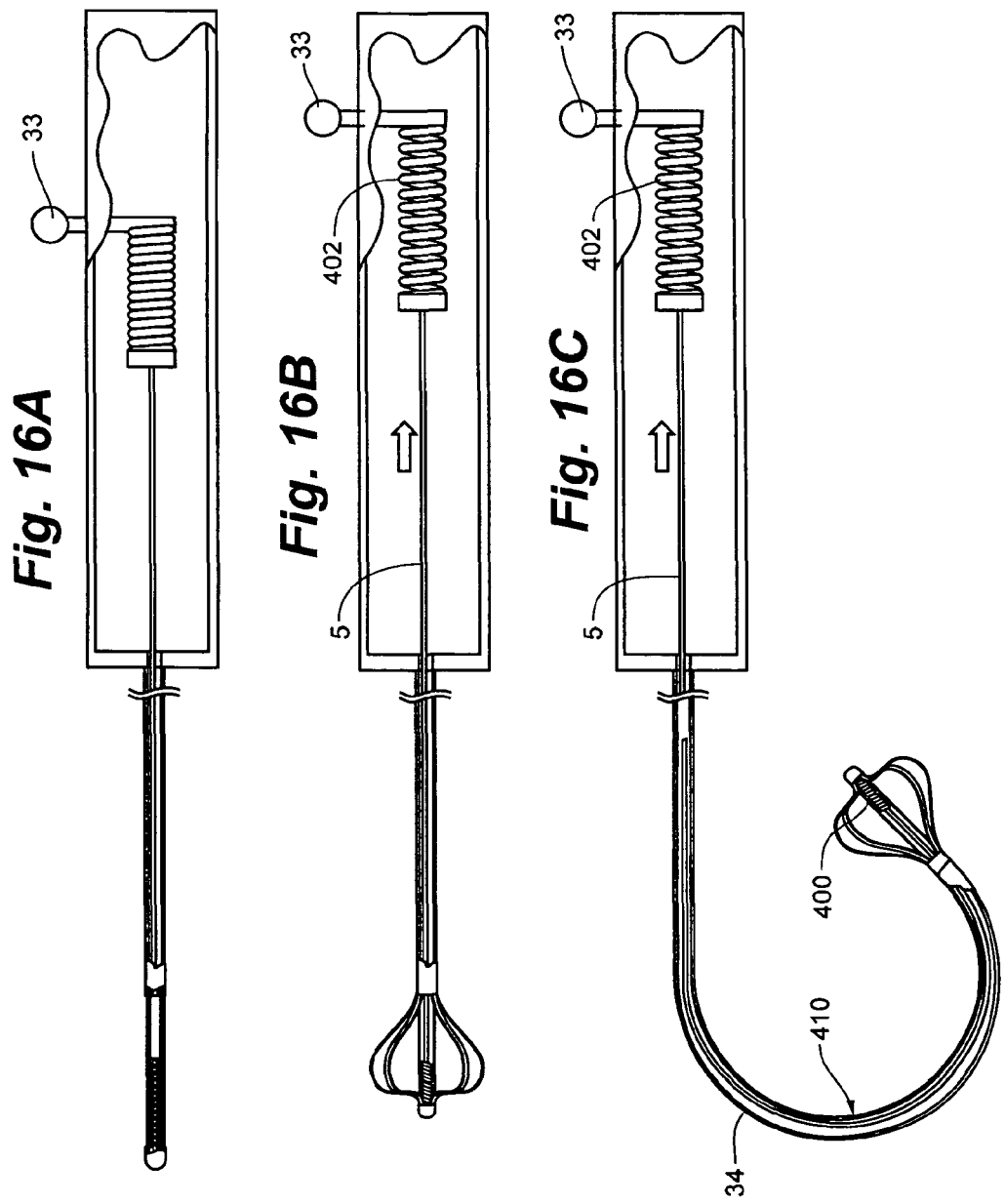

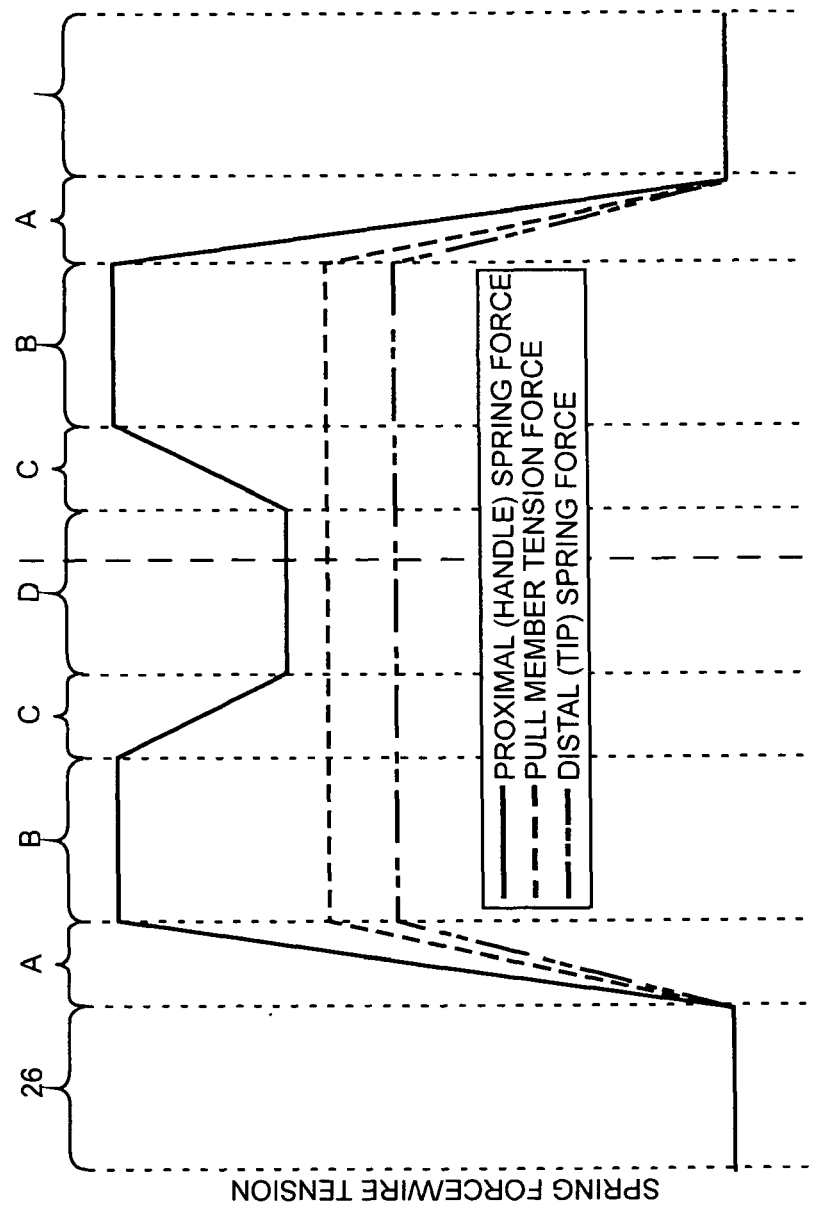

CARDIAC MAPPING CATHETER

CROSS-REFERENCE TO RELATED APPLICATIONS

This application is a continuation application and claims priority under 35 U.S.C. §120 to U.S. patent application Ser. No. 13/289,367, filed on Nov. 4, 2011, now U.S. Pat. No. 8,447,377, which is a continuation of U.S. patent application Ser. No. 12/005,975, filed on Dec. 28, 2007, now U.S. Pat. No. 8,103,327, the entire contents of which are hereby incorporated by reference.

FIELD OF THE INVENTION

The present invention relates generally to a catheter for use inside the human heart during medical procedures. The catheter can be used for "non-contact" mapping of the electrical activity of the heart, for locating and reporting the position of other procedure catheters within the heart, and for other purposes. The catheter includes an electrode array that can be deployed and retracted independently from catheter articulation.

BACKGROUND OF THE INVENTION

Cardiac arrhythmias are a leading cause of stroke, heart disease, and sudden death. The physiological mechanism of arrhythmia involves an abnormality in the electrical conduction of the heart. There are a number of treatment options for patients with arrhythmia that include medication, implantable devices, and catheter ablation of cardiac tissue.

Traditionally, the arrhythmia is studied and diagnosed by "electrically mapping" the heart with catheters inserted through the vasculature into a heart chamber. Traditionally, the electrical activity of the heart is acquired directly by "in-contact mapping" of the interior wall surface of a heart chamber. In this technique electrodes are placed in intimate contact with the heart wall and the voltage at that location is recorded and plotted against time for display to the physician. The in-contact catheters may be large and essentially fill the entire heart chamber, or they may be smaller and moved around in the heart chamber to sequentially map various areas of the heart. Mechanically, the in-contact mapping catheters are "soft" so that they can conform to the heart chamber. Softness is required so the electrodes come into intimate contact with the heart wall while accommodating wall motion of the beating heart.

For example, multiple electrode in-contact mapping catheters are known from U.S. Pat. No. 5,628,313 to Webster that shows a so-called "basket" catheter. In use, this very flexible and conformal catheter is deployed in the heart and presses individual electrodes against the chamber wall for full chamber contact mapping of a beating heart. Smaller multiple electrode catheters are known as well. For example, the U.S. Pat. No. 5,279,299 to Imran illustrates techniques for creating smaller catheter arrays that are used to selectively contact map portions of the cardiac chamber. This catheter is flexible and electrodes remain in contact with the wall even when the catheter shaft is displaced slightly. In each of these examples, the limbs of the catheter are very flexible and gently contact the chamber wall while the wall of the heart is moving.

"Non-contact mapping," also known in the art, is an alternative to in-contact mapping where a catheter array positioned within a chamber is used to collect global electrical information. This global information is then used to compute a solution to the so-called "inverse problem". The inverse problem of electrophysiology is the calculation of wall electrical potentials from the measured field voltages associated with the wall potentials as measured within the blood pool remote from the chamber wall. The mathematical "solution" displayed to the physician is the computed wall surface voltages that can be used to detect problems in electrical conduction in the heart wall.

Although in-contact and non-contact catheters are used for the same patient indications, they have very different mechanical and electrical requirements. Chief among the requirements of a non-contact catheter is stability of the electrode array. The geometry and locations of the electrodes are assumed for the inverse solution calculation and need to be known with great precision. Small error in electrode position can render large discrepancies in computed mathematical solution. In addition, controlled movement of the electrode array within the chamber of interest is necessary in order to improve the accuracy of the non-contact map. Deployment of the electrode array into a repeatable precisely known shape, while supporting controlled movement of the catheter, pose particularly complex and novel requirement on the catheter design.

Once the anatomic origin of problems in electrical conduction are identified, the physician may proceed to ablate the offending tissue, thus treating the arrhythmia. Catheter ablation procedures have evolved in recent years to become an established treatment for patients with a variety of supraventricular and ventricular arrhythmias. The typical catheter ablation procedure involves mapping of the heart tissue in order to identify the site of origin of the arrhythmia, followed by a targeted ablation of the site with an RF catheter. The procedure takes place in an electrophysiology laboratory and takes several hours most of which is spent mapping the electrical conduction in the heart.

Although in-contact and non-contact mapping methods are known in the art and various deflectable, displaceable and deployable catheters are known as well, there is a continuing need to improve the accuracy, stability and maneuverability of such devices so that they can be more widely used, especially as an adjunct to cardiac ablation procedures.

SUMMARY OF THE INVENTION

The present invention is an intravascular catheter that may be deployed within a heart chamber placing multiple electrodes in a known spatial configuration. The catheter may be used to map electro-anatomical characteristics of the heart and/or to locate and position other catheters within the heart. Adoption of the inventive construction of the present catheter provides a device that is smaller, less expensive to manufacture, maneuverable, and stable in its deployed configuration. Electrode stability makes the device much more accurate and therefore, of more value to the physician. The design and construction also make the device smaller in cross section than existing designs and therefore, more easily used by a physician and better tolerated by the patient. As set forth in detail hereafter, the distal array of the catheter is fabricated as a flexible printed circuit. The deployment and articulation functions of the catheter are very independent of each other.

Two separate embodiments of the deployment mechanisms are disclosed. In contrast to prior art devices both of these mechanisms permit the deployment function to operate wholly independently from the articulation or deflection feature of the catheter. The independence of the deployment feature and the articulation feature together with innovative structural features and materials create a noncontact mapping catheter that is easily placed and used with a very stable electrode geometry.

BRIEF DESCRIPTION OF THE DRAWINGS

An illustrative embodiment of the invention is shown in the several views of the figures. The use of identical reference numerals throughout the several figures and views indicate the same element of the device, wherein;

FIG. 2A is a schematic diagram showing the catheter;

FIG. 2B is a schematic diagram showing the catheter;

FIG. 2C is a schematic diagram showing the catheter;

FIG. 4A shows a step in the construction of the distal portion;

FIG. 4B shows a step in the construction of the distal portion;

FIG. 4C shows a step in the construction of the distal portion;

FIG. 4D shows a step in the construction of the distal portion;

FIG. 5A shows a step in the manufacture of the distal portion;

FIG. 5B shows a step in the manufacture of the distal portion;

FIG. 7 shows a metallization layer of the flexible printed circuit;

FIG. 7A shows a portion of the metallization layer of the flexible printed circuit of FIG. 7;

FIG. 7B shows a portion of the metallization layer of the flexible printed circuit of FIG. 7;

FIG. 7C shows a portion of the metallization layer of the flexible printed circuit of FIG. 7;

FIG. 8A shows the spline assembly formed from a flexible printed circuit in plan view;

FIG. 8B shows the spline assembly formed from a flexible printed circuit in cross-section view;

FIG. 8C shows a distal array segment in projection view;

FIG. 8D shows a spline in cross section;

FIG. 8E depicts a portion of a spline of FIG. 8D;

FIG. 9A shows the spline assembly formed from a flexible printed circuit in plan view;

FIG. 9B shows the spline assembly formed from a flexible printed circuit in cross-section view;

FIG. 9C shows a distal array segment in projection view;

FIG. 9D shows a spline in cross section;

FIG. 9E depicts a portion of the spline shown in FIG. 9D;

FIG. 10A shows a first embodiment of the deployment actuator;

FIG. 10B shows a first embodiment of the deployment actuator;

FIG. 15 shows simplified schematic of second embodiment of the deployment actuator showing complimentary distal and proximal springs;

FIG. 15A shows a portion of the actuator of FIG. 15;

FIG. 16A is a simplified schematic of the catheter;

FIG. 16B is a simplified schematic of the catheter;

FIG. 16C is a simplified schematic of the catheter; and,

FIG. 17 is a plot of force against displacement of several structures in the catheter.

DESCRIPTION OF THE INVENTION

Figure 1:
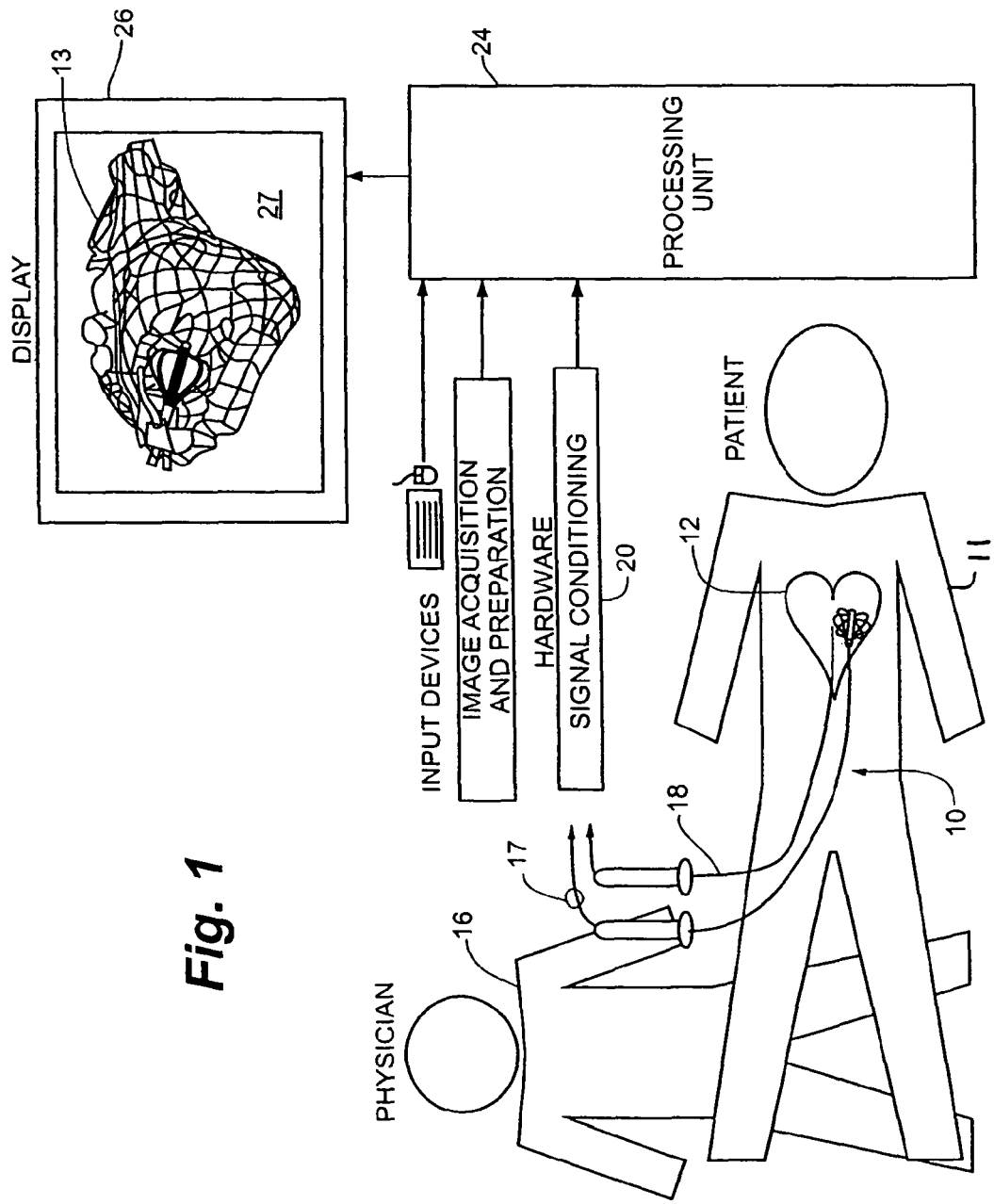
FIG. 1 is a schematic diagram showing the catheter in the context of the system.

FIG. 1 depicts the context of the invention. The figure shows a highly schematic view of the overall system that includes the physician, patient, catheters, and related electrophysiology equipment located within an operating room. The physician 16 introduces the catheter 10 into the vasculature of the patient 11 at the patient's leg and advances it along a blood vessel ultimately, entering the patient's heart 12. Other catheters that may be used in the procedure are represented by companion catheter 18. Each catheter is coupled to signal conditioning hardware 20 with appropriate catheter cabling typified by catheter cable 17. The signal, conditioning hardware 20 performs various interface functions applicable to the mapping, tracking, and registration procedures that are performed in conjunction with the workstation class computer-processing unit 24. If the companion catheter 18 is an ablation catheter, then conditioning hardware also forms an interface to an RF ablation unit (not illustrated). Three patent applications all published Dec. 27, 2007 are incorporated by reference herein to further explain the use of the catheter for non-contact mapping as follows: 20070299353; 20070299352 and 20070299351.

In use, the physician looks at a computer display 26. Present on the display is a substantial amount of information. A large window presents an image of the heart chamber 13 along with an image of the catheter 10. The physician will manipulate and control the catheter 10 based in part on the images and other data presented on the display 26. The image 27 seen in FIG. 1 is schematic and depicts the distal array of the catheter 10 deployed, occupying a small portion of the heart chamber 13 volume. The representation of the heart chamber 13 may use color, wire frame, or other techniques to depict the structure of the heart chamber 13 and to simultaneously portray electrical activity of the patient's heart. It is regarded as useful to display chamber geometry, catheter location, and electrical activity in an integrated fashion on the display 26. In use, the physician will observe the display 26 and interact with the workstation processing unit 24 and the catheters 10 and 18, to direct the therapy as a medical procedure.

FIG. 2 A through FIG. 2 C depicts array deployment and catheter articulation along with the associated positions of the handle controls. FIG. 2A shows the catheter in isolation. The catheter 10 has an elongate body 31 with a distal end 37 and a proximal end 39. The elongate body 31 includes a tubular sheath 35. The proximal end 39 connects to an assembly that includes a handle segment 30. The physician may manipulate the handle segment 30 to selectively deflect, deploy, and rotate the catheter to perform the medical procedure. The handle segment 30 is coupled to an elongate intermediate section or segment 32. The intermediate section is coupled to a deflection segment 34, which in turn is coupled to a distal array segment 36, located at the distal tip or end 37. Not shown is the catheter cable 17 used to connect the electrodes on the distal array segment 36 to the signal conditioning hardware 20. In FIG. 2A the catheter 10 is in the undeflected and undeployed state where the distal array segment 36 is collapsed and the deflection segment 34 is straight. In this configuration, the catheter is introduced into the body using the familiar Seldinger technique.

FIG. 2B shows the catheter 10 with the handle segment 30 manipulated to deploy the distal array segment 36 into the open or deployed state. In one embodiment, the pommel 33 of the handle assembly 30 is moved retrograde with respect to the handle assembly as indicated by motion arrow 38 to deploy the distal electrode array segment 36. In this embodiment, the pommel 33 will lock into position to deploy the array 36. To set the lock, the pommel 33 will have to be pulled enough to overcome a modest spring force to reach a detent position. When deployed, the distal array segment 36 opens to place electrodes into the operating position. In alternative embodiments the deployment control may be turned or rotated to deploy the electrode array.

FIG. 2C shows activation of the deflection segment 34. Antegrade motion of the handle ferrule 42 of the handle segment 30 depicted by motion arrow 40 deflects or articulates the deflection segment 34. Note that the catheter 10 responds to this motion and the deflection segment 34 forms an arc confined to a single plane. In the figure, the articulation or deflection motion lies in the plane of the page. The deflection operation causes the distal array segment 36 to be pointed up to 180° from the initial direction shown in panel 2A. The phantom dotted position seen in the figure shows that this articulation may be symmetrically "bi-directional." It should also be understood that the articulation may also be asymmetrically bi-directional such that the arc shape is different in each direction. In one embodiment, best depicted in FIG. IS, articulation or deflection of the segment 34 moves a pull wire from the center axis of the catheter and it moves off to the side within the catheter body. This displacement of the pull wire reduces tension in the pull wire and leads to the deflection.

Thus it is shown that the catheter 10 has an elongate body 31 having a distal end 37, and a proximal end 39, and an elongate central axis. A proximal handle segment 30 having an articulation control 42 and a deployment control 33 are attached to the proximal end 39. There is an intermediate segment 32 connected to the handle and a deflectable segment 34 connected to the intermediate segment 32. The deflectable segment 34 will articulate in a plane through an angle in response to the articulation control. Also a distal array segment 36 is connected to the deflectable segment 34. This distal array segment 36 includes a deployable distal electrode array that can move from a first retracted position depicted in FIG. 2A to a second deployed position depicted in FIG. 2B. The deployment mechanism coupled to said deployment control couples the motion of the deployment control to operate the distal electrode array segment which causes the distal array segment to deploy into said second deployed position, independently of the operation of said articulation control.

The physician can rotate the handle segment 30 and operate ferrule 42 to position and "aim" the distal array segment 36 toward any part of the cardiac anatomy within the heart chamber. When deployed, the various splines typified by spline 50 carry various electrodes into specific highly stable and reproducible spatial locations.

Figure 3B:
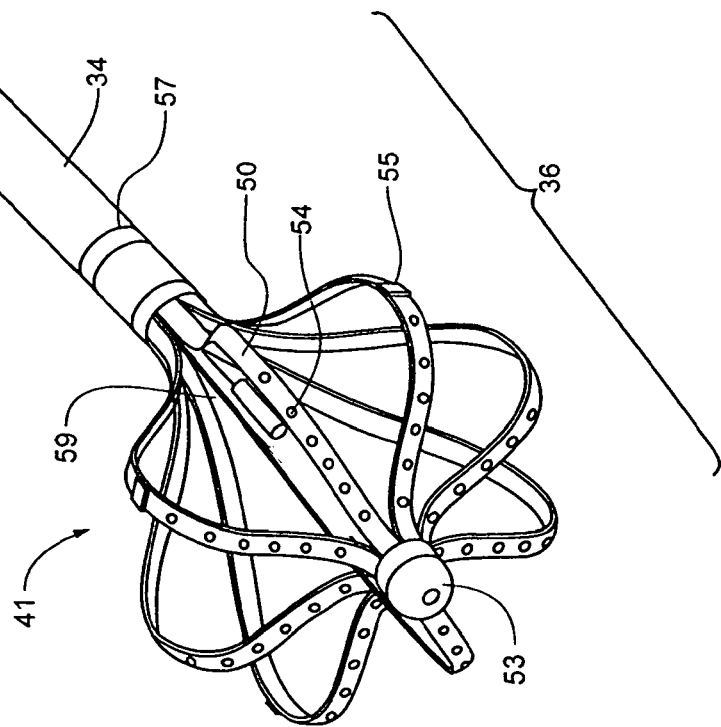
FIG. 3B is a schematic diagram showing the distal portion of the catheter.
Figure 3A:
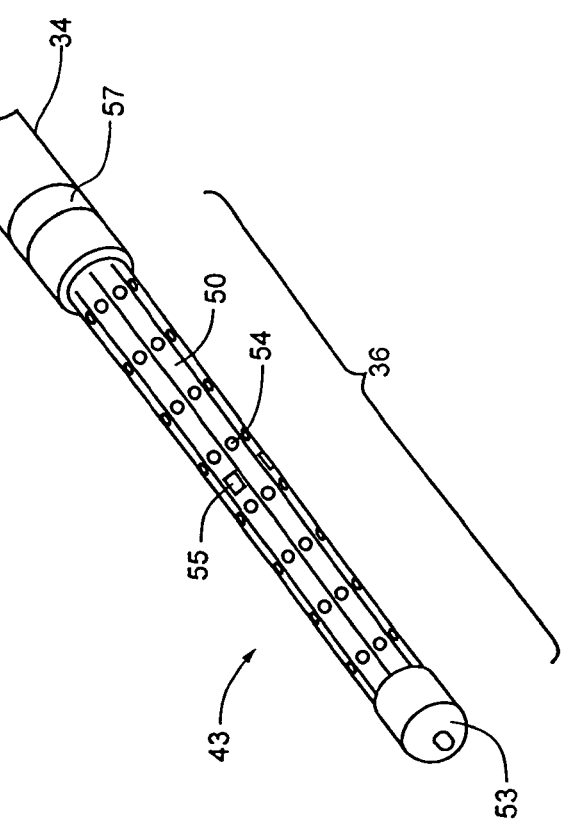
FIG. 3A is a schematic diagram showing the distal portion of the catheter.

FIG. 3A and FIG. 3B depict the distal array segment 36 in the deployed and undeployed states and serve to illustrate the location of the electrodes. FIG. 3A shows the distal array segment 36 in isolation and in the retracted or undeployed 43 state or condition. The drawing shows a uniform and symmetrical distribution of the electrode sites as typified by electrode 54 along the length of a typical spline 50. It may be useful to place more of the sensing electrodes near the most distal end or tip 37 of the distal array segment 36. An asymmetrical electrode distribution may be advantageous for non-contact mapping functions. In addition to multiple sensing electrodes, current injecting locator electrodes, typified by locator electrode 55, may be placed at a location along the spline 50. In general it is preferred to position locator electrodes so that they are far apart in the deployed sate. Current sourcing or sinking for the locator electrodes may also take place from ring electrodes 57 and tip electrode 53. Tip electrode 53 may also be provided for cardiac stimulation, ablation or as a locator electrode.

In summary, the splines 50 of the distal electrode array segment 36 may carry various sets of independent electrodes 54. Typically sixty-four sensing electrodes will be distributed over and along the various splines 50. Several locator electrodes may be positioned diametrically opposed to each other as illustrated by example, on the meridian of the deployed shape. Optionally other electrodes may occupy space in the distal electrode array. In use, sets of the electrodes are used at various times or concurrently during the medical procedure.

FIG. 3B shows the distal array segment 36 in the deployed state 41. Together FIGS. 3A and 3B show the motion of the several splines that make up the distal electrode array 36 as they move from the undeployed state 43 to the deployed state 41. While in the undeployed state 43, the splines lie together along side each other in a roughly tubular shape seen in FIG. 3A. The splines typified by spline 50 deflect and blossom moving outwardly in a radial direction as the array is deployed to the deployed state 41 as seen in FIG. 3B. This spline motion may be driven by a pull wire (FIG. 15 element 52) in a pull wire embodiment. Alternatively the spline motion may be driven by a rotating screw 153 that moves the screw driven pull member 159 seen within the array in FIG. 10A and 10B. A rotatable member is used as a torque transmitting device from the handle to the screw member in the distal section. The rotatable member needs to be able to transfer torque while in a curved environment. The rotatable member can be implemented in the form of a torque transmitting wire, coil, braid reinforced plastic tube or laser cut hypotube. The term rotatable member is intended to describe all of these alternative constructions. This alternative embodiment is called the rotary screw embodiment.

In the pull wire embodiment, the pull wire 52 is pulled back into the catheter body of the deflectable segment 34 and the splines deform into a shape reminiscent of a bulb of garlic. The pommel control 33 and the proximal spring 402 are connected to the pull wire 52 and motion of the pommel control 33 moves the splines to the deployed state.

The individual splines may carry several types of electrodes. The array of sensing electrodes typified by spline electrode 54 are used for non-contact mapping and may also be used for assisting in the detection and location of companion catheters in the heart chamber. These non-contact electrodes are in the blood pool and they must receive and detect very small voltages to perform the mapping operation. Locator electrode 55 is typical of such a spline electrode used for location purposes (also shown in FIG. 3A). Typically locator electrodes will lie on the greatest meridian of the deployed array 41 so that once deployed they are quite far from each other as seen in FIG. 3B. However not every spline need carry a locator electrode.

Each electrode on a spline is electrically connected to the cabling in the handle. It is preferred that the signal from each individual electrode be independently available to the hardware interface 20. This may be achieved by passing a conductor for each electrode through the connection cable 17. As an alternative, the electrical connections may be multiplexed in the catheter device 10 to minimize conductors.

It is important that the high-density electrode array be deployed into a known, reproducible, and relatively stiff shape. The number of electrodes, their distribution and deployment shape, and stability in shape determine the limits of system performance. As electrode number and deployment volume increase, the performance is improved. However it is both difficult and important to balance complexity, cost, and performance with usability and patient benefit. An increase in electrode number and deployment size increases catheter 10 complexity and maneuverability of the catheter 10 is compromised. Experimental work suggests that a typical catheter 10 should have sixty-four sensing electrodes and deploy to a three dimensional somewhat spherical shape with a diameter of 18 mm. In order to know electrode locations for analysis by the processing unit 24, the deployment shape must be tightly controlled. Therefore, several critical design features must be tightly controlled. The location of the electrodes 54 within the array must be accurately placed. These electrodes 54 should also be placed in a manner that facilitates their use in close proximity to the endocardial surface when the array is deployed. This requirement may necessitate a non-uniform distribution of the electrodes 54 as certain regions of the deployed array are more likely to be positioned closely to the endocardium.

The deployed shape of the electrode array must be repeatable through multiple deployment cycles. For example, electrode locations need to be known to within 1 mm between multiple deployments. The array should be capable of deploying to a known shape and subsequently dosing to a low profile (e.g. 8 French) for retraction. This shape change may be binary or continuous, but in either situation, the shape must be repeatable and have a known geometry at the time of data collection. The repeatable shape requirement is applicable to the electrode array shape in both the circumferential and radial directions and represent a significant design challenges. The inventive combination of fabrication technology, structural design and material choices cooperate together to achieve the design goal.

Also seen in FIG. 3B is a locator sensor 59. There are several commercially available 3-D location systems available for use in medical devices. In general location of the locator sensor 59 in space is reported by a base station located near the patient. This technology is widely used in robotic surgery and need not be described in detail. Typically the locator sensor 59 would take the place of locator electrode 55.

FIG. 4A through FIG. 9D depict the formation of the array structure from a flexible printed circuit.

FIG. 4A shows a step in a preferred construction methodology for the distal array segment 36. The distal array segment 36 is manufactured in part from a flexible printed circuit 60 ("FPC"). This construction methodology has the advantage of repeatable high accuracy and low manufacturing cost. To construct the FPC 60, the material is initially fabricated in a planar form seen in FIG. 4A. In the planar condition, a series of apertures 62 are cut through the FPC 60 at one end typified by hole 62. Together the series of apertures 62 form a bonding band 70. At the opposite more proximal end of the FPC 60 there is formed a termination band 106. The planar FPC 60 is also slit to free the individual splines. Conventional laser processing is well suited to this fabrication step.

FIG. 4B shows a process where the planar FPC 60 is wound around a major axis 61 bringing first edge 63 toward second edge 65.

FIG. 4C shows the two edges juxtaposed with both ends fixed. Together the bonding band 70 and the termination band or section 106 complete a cylindrical form. In general the distal bonding band 70 is fixed by encapsulation and the termination band is fixed by anchoring or bonding it to the deflection segment of the catheter.

FIG. 4D shows that with both ends fixed, the splines typified by spline 50 may be moved radially with respect to the axis 61.

FIG. 5A shows that the ring of apertures 62 that together from a bonding band 70. In the figure, the edges of the gap are seen in close proximity at reference numeral 72.

FIG. 5B shows the use of the bonding band 70. Note that the edges may be held together with a melted polymer or adhesive or other plastic or thermoplastic material that is applied to the interior and exterior of the tubular structure. This thermoplastic formed-in-place plug 74 encapsulates the inside and outside of the FPC 60 providing an unusually robust and durable structure that permits reliable deployment of the splines.

Figure 6A:
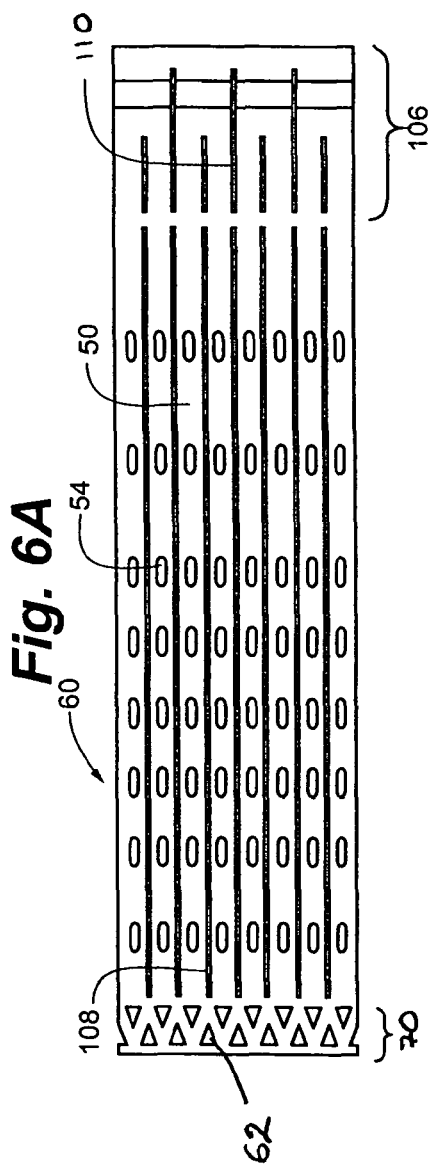
FIG. 6A shows the flexible printed circuit in plan view.

FIG. 6A shows the FPC 60 in plan view. This view reveals the several slits typified by slot or slit 108 which taken together form the individual splines such as spline 50. These slits 108 extend from the distal bonding section or band 70 to the termination section 106. Holes 62 appear in the bonding band 70 and additional slits 110 are formed within the termination section 106 to facilitate attachment to the deflectable section of the catheter.

The splines typified by spline 50 of the FPC 60 serve to position the electrodes typified by electrode 54 along the length of the FPC 60. The splines 50 also carry interconnecting metal traces (not shown) that serve to electrically connect the electrodes to pads in the termination section 106. The splines 50 are separated from each other using slits 108. The slits are thin gaps that are cut in the FPC using one of many cutting techniques that may include laser cutting, die cutting or chemical etching. The slits 108 of the exemplary FPC are cut using a laser so as, to position slit location precisely.

The distribution of the electrodes 54 may be tightly controlled in the design of the FPC 60. For example, in FIG. 6A we note that electrodes are distributed more densely in the distal tip area. It should be appreciated that any desirable electrode distribution may be accomplished using this method.

Figure 6B:
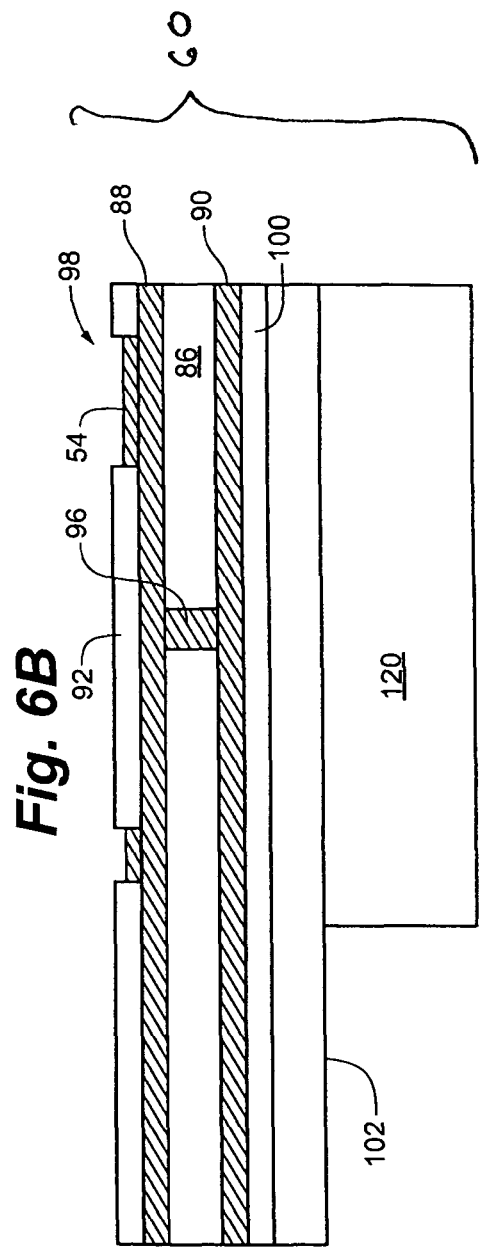
FIG. 6B shows the flexible printed circuit in cross-section.

FIG. 6B shows the FPC 60 in cross-section. The various layers are not to scale. Some layers described are very thin while other thick, not all layers are depicted in the figure for clarity. In particular, very thin layers are not shown explicitly in the drawings. The FPC is constructed using a relatively thick core insulating layer 86. The core layer 86 of the exemplary circuit is constructed of a 50 um layer of polyimide. Alternative materials and thickness core layers may be used to obtain the desired mechanical and process characteristics. The core insulating layer 86 is coated with a top metallization layer 88 and a bottom metallization layer 90. Each of the exemplary metallization layers is deposited by first sputtering a thin layer (~0.1 um) of titanium over the core insulating layer 86. The titanium layer serves as an interface layer to adhere additional metallization to the core insulating layer 86. The metallization layers 88 and 90 can be added by further sputtering and/or plating of additional metal over the titanium layers. The exemplary metallization layers 88 and 90 are sputtered with a gold layer over the titanium layer and then further plated with gold until the total thickness of the metal layers measures 2 um. It should be noted that other conductors such as copper may also be used. It is also necessary to provide electrical connection between metal layers 88 and 90 for the purpose of connecting circuit features that reside on each layer. A connection can be formed by constructing a via 96 between the two metallization layers. A via can be formed by creating a hole through both metallization layers 88 and 90 and the core insulating layer 86. Electrical connection is then made by plating the walls of the hole between the two metallization layers forming a metal connection 96 between the metallization layers 88 and 90. The FPC is further constructed by providing a top covercoat 92 over the top metallization layer 90. The top covercoat 92 serves to insulate portions of the top metal layer 88 from external contact. The top covercoat has openings 98 placed in regions where it is desired to have the top metal layer exposed to external contact. For example a mapping electrode 54 may have the covercoat above it exposed and be sputtered or plated onto the top metal layer 88 as seen in FIG. 6B.

In the exemplary construction of FIG. 6B, the covercoat 92 of the FPC is formed by a 25 um layer of liquid photoimageable polyimide. The photoimageable polyimide covercoat is exposed and developed to precisely locate geometric features on the exterior surface to create blood contacting electrodes, using similar registration and optical techniques used to fabricate other features on the FPC.

A bottom covercoat 100 is applied to the bottom metal layer 90 in order to insulate the bottom metal layer 90 from external contact. It may be necessary in some applications to enable the bottom covercoat 100 to have openings similar to the openings 98 of the top covercoat 92. Such applications may require external contact to the bottom metal layer 90. One important application for the mapping electrodes 54 is to sense low voltage biological signals. The biological signals of interest are generally in the tens of microvolts to several millivolt range in amplitude and are time varying in the frequency range of 0.05 Hz to several kHz. The detailed design of the Flexible Printed Circuit (FPC) layers and electrodes in particular impact the noise level of the measurement system. Reducing the impedance of the electrochemical interface between the electrode and blood reduces overall system noise.

Although a wide range of materials may be used to reduce impedance, our preferred electrode materials are selected from a small group which have demonstrated to us that they are especially well suited for this design. We prefer to select electrode materials for blood contact from the group of gold, stainless steel, platinum, platinum-iridium, titanium nitride, platinum black or iridium oxide (in order of highest to lowest impedance). Electrode materials are applied using an electroplating or sputtering process.

At present our preferred FPC 60 and electrode construction includes an FPC with a polyimide core layer with gold metal layers. The blood contacting electrodes are gold coated with iridium oxide.

In addition to material properties, electrode area has a profound impact on impedance and in the design the electrode area may be increased to a width limited by the dimension of the spline and further limited by the presence of other metal features including traces.

It is also be possible to increase the surface area of electrodes through surface finishing. Roughening of the electrode surface can be accomplished through anyone of several mechanical or chemical surface treatments.

FIG. 6B also shows that a stiffener layer 102 may be applied over the bottom cover coat 100 as seen in FIG. 6B. The stiffener layer 102 may have various thickness and material compositions in order to achieve the desired rigidity of the FPC in order to control the deployed shape. The exemplary FPC of the invention is comprised of a 50 um thick polyimide stiffener 102 over the bottom covercoat 100. It should be appreciated that other materials such as PEEK or Nitinol may be used as a stiffener. The stiffener 102 is adhered to the to the bottom covercoat using a polyimide adhesive layer. Other adhesives, and in particular, pressure sensitive adhesives may also be used for this purpose. Additional stiffener layers may be applied over stiffener layer 102. Stiffener layer 120 serves to increase the stiffness of the circuit in selected areas.

The termination section 106 also serves to provide a region where the FPC may be bonded to the outer catheter shaft during installation.

FIG. 7 shows a metallization layer in plan view. The dark areas in FIG. 7 are the metallization traces created by the processes described in connection with FIG. 6A, but the core layer and other layers are not shown for clarity. Subpanels seen in the figure are enlargements of the metallization trace pattern to show various features. For example, the termination section 106 of the FPC of FIG. 6A is shown as traces 108 in this figure. The traces are metallic layers that serve to create a region where the FPC can be connected to wire or cabling that serve to electrically connect the FPC to circuitry or connectors in the proximal section of the catheter. The wire or cabling may be attached to the FPC at a series of termination lines as designated by reference numeral 112.

It should be appreciated that a number of metallization layers ranging from 1 to 16 may be used. The addition of layers is helpful in carrying additional signals given a width constraint such as the spline width.

FIG. 8A shows how to increase the stiffness of the exemplary FPC of FIG. 6 forming areas of high stiffness 124 and areas lower stiffness 126.

FIG. 8B shows how to control the deployed shape of the array by controlling the stiffness of the exemplary FPC forming areas of high stiffness 124 and areas of lower stiffness 126.

FIG. 8C shows a representative shape where stiff zones 124 or areas interspersed with less stiff areas 126 can create a complex array shape upon deployment. In the figure, there is more stress in the thin areas 126 which bend more readily than in the stiffer regions 124.

FIG. 8D shows thicker regions with additional stiffener layers forming stiff zones 124 while less stiff material yields a less thick more flexible area 126. The use of alternating stiffness areas helps to control the distribution of stress as well as determine deployed shape. In this embodiment the spline shape is segmented into relatively rigid "straight" sections 124 followed by "hinged" areas 126. The detail drawing of FIG. 8E shows the high stiffness area 124 next to a lower stiffness area 126.

FIG. 9A shows how to increase the stiffness of the exemplary FPC of FIG. 6 forming areas of high stiffness 124 and areas of lower stiffness 126 that are spaced along the spline.

FIG. 9B shows that a stiffener layer 102 may be applied over the bottom covercoat 100 as described in connection with FIG. 8B.

FIG. 9C shows a representative shape where stiff zones 124 or areas combined with less stiff areas 126 can create a complex array shape upon deployment. In the figure there is more stress in the thin areas that bend more readily than in the stiffer regions 124. Together the added material allows for a smoothly varying distribution of stress along the spline.

FIG. 9D shows thicker regions with additional stiffener layers forming stiff zones 124 while less stiffener material yields a less thick more flexible area 126. The use of alternating stiffness areas helps to control the distribution of stress as well as determine deployed shape yielding a continuously curved spline having a smoothly varying distribution of stress along the spline. The detail drawing in FIG. 9E shows a stiff area 124 next to a less stiff area 126.

Thus it is shown that distal deployable electrode array segment is formed from a multiple layer flexible printed circuit slit to form splines and rolled about said longitudinal central axis to form said distal electrode array The slits may be wider or narrower along the length of the spline and this non-uniform shape characteristic results in control of the shape of the electrode array in the deployed position. It should also be appreciated that the stiffer elements along the splines also create a non-uniform shape characteristic that results in control of the final shape of the electrode array in the deployed position or state.

To provide the physician with visual feedback of the array state (deployed or undeployed), the array needs to be visible on fluoroscopy. This may be accomplished in several ways. The circuit may be made from and enhanced with an additional layer made from materials that are, in themselves, radiopaque such as gold, platinum, and/or tungsten, including others. Alternatively, a radiopaque substrate can be added to the array to enhance visualization upon deployment. This substrate can be in the form of marker bands, coiled wire, or radiopaque ink. In particular, the radiopaque ink may contain suspended tungsten that has radiopaque properties. This type of ink could be applied through a printing process on the undeployed electrode assembly while in the FPC configuration.

Figure 13:
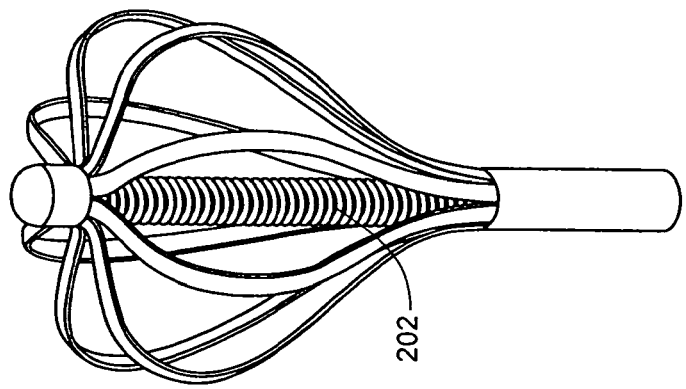
FIG. 13 shows a distal array segment in projection view
Figure 12:
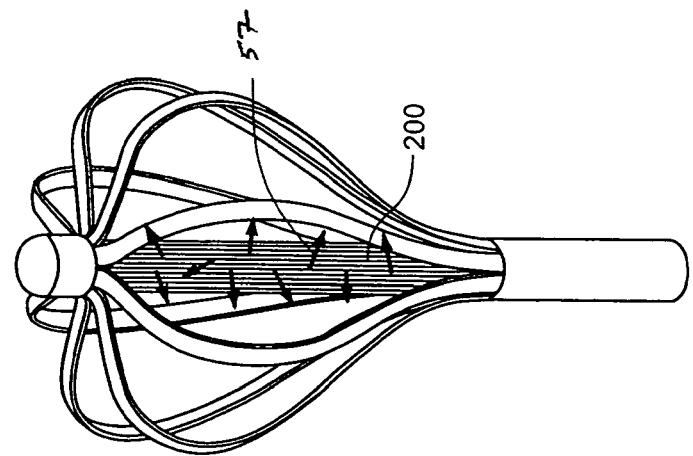
FIG. 12 shows a distal array segment in projection view.
Figure 11:
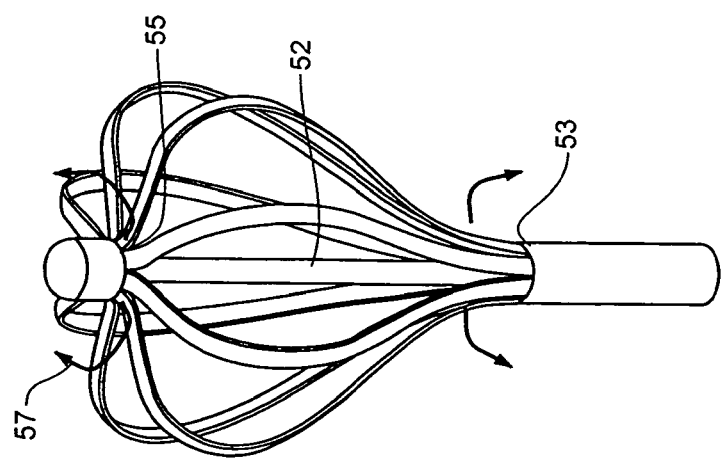
FIG. 11 shows a distal array segment in projection view.

FIG. 11, FIG. 12, and FIG. 13 show differing strategies to reduce blood clotting on the array. It is conventional practice to administer anticoagulants to a patient undergoing these procedures. However is very useful to eliminate blood clotting on the catheter itself FIG. 11, FIG. 12, and FIG. 13 show several techniques that may be adopted to achieve this goal. Continuous or episodic injection of saline or heprinized saline are contemplated with the embodiments of FIG. 11 and FIG. 12. It should be noted that various coating such as hydrophilic coatings, hepirnized coatings, and parylene may also be applied to catheter surface alone or in combination with the techniques presented in the figures in order to reduce clot.

FIG. 11 shows a distal segment having a fluid supply lumen associated with the pull wire feature 52. Fluid 57 introduced into a hub at the proximal end of the catheter emerges from aperture 53 and aperture 55 to flood the array and prevent blood clots from adhering to the splines.

FIG. 12 shows a porous membrane associated with the pull wire feature location in the distal array segment to allow fluid introduced into the catheter under pressure to emerge from the porous sheath 200 and flood the array to prevent blood clots from adhering to the splines.

FIG. 13 shows a collapsible corrugated section 202 preventing blood from entering the catheter opening in the distal array structures.

Figure 14:
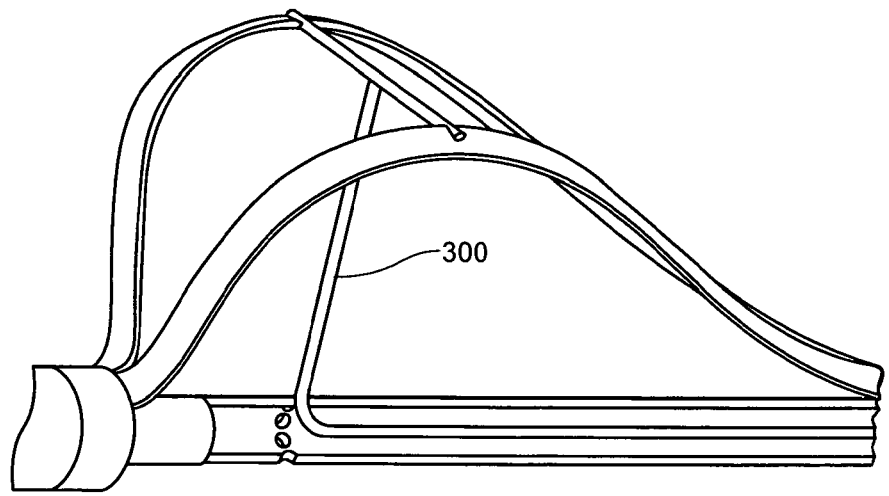
FIG. 14 shows a partial section of a distal segment with an additional feature.

FIG. 14 shows a strategy for constraining the deployment providing tight control over the final shape of the deployed array. For example tether 300 may emerge from the central shaft in FIG. 14 to restrain the motion of the splines or limbs.

As described previously, it is or great importance for the catheter to support controlled articulation while keeping the deployed shape known. FIG. 15 and FIG. 10 describe two different embodiments that meet this requirement. The mechanism in FIG. 15 relies on a spring to accomplish independence of the two mechanisms, while the mechanism of FIG. 10 relies on threads in distal array segment 36 to accomplish the same goals.

FIG. 15 is a simplified schematic diagram of the catheter that serves to describe the interaction between the articulation and deflection aspects of the catheter. The figure serves to explain the operation of one embodiment of the array deployment construction. In brief, the array is pulled open with a pull wire. The array is biased by a spring 400 to return to the undeployed state. The pull wire 52 extends from the handle 30 where it is anchored to a proximal spring 402 to the distal tip 37 where it is anchored in the distal tip. The proximal spring 402 is in turn connected to the pommel or deployment control 33. As the deployment control 33 is retracted the pull wire pulls the distal tip 37 toward the handle 30. The tip motion is guided by tube 406 sliding over a bushing 408. This motion can continue until the tube bottoms out on surface 404. This mechanical stop determines the amount of shortening of the distal segment. As a consequence this stop also serves to limit the deployed state of the deployable array. In this figure the splines are not shown for clarity (for comparison see FIG. 16B). This motion also compresses the distal spring 400. If tension of the pull wire is eased then the distal spring 400 restores the array to the undeployed state.

The pull wire 5 and the proximal compensator spring 402 have a nominal length that gets longer or increases as the deployment control moves into the locked position. The increase in length comes from the tension supplied to the spring that increases spring length. This process is seen dearly comparing FIG. 16A to FIG. 16B.

FIG. 16C corresponds to deflection or articulation of the catheter deflectable segment 34. The deflection control causes the catheter to deflect in the plane of the figure and this displaces the pull wire 52 within the elongate catheter body 32. As the pull wire moves from a concentric to an offset position within the body 34 the relative length of the pull wire compared to the length of the shaft changes. This is seen most clearly at reference numeral 410.

The proximal spring 402 compensates for and takes up this motion by contracting slightly while still providing enough tension in the pull wire to keep the distal array fully deployed.

FIG. 17 shows the interplay of tension in the pull wire and displacement of catheter components. As the control 33 is activated and moved toward the deployed condition, tension rises in the wire as seen at panel A. When the array is full deployed the mechanical stop engages the proximal spring and force preferably remains constant as the control reaches the deployed state depicted in panel B. In this state, the catheter is in the state depicted in FIG. 16B. During deflection, as seen in FIG. 16C, the relative motion of the pull wire and its housing causes the spring tension to falloff in the proximal spring as seen in panel C to D, while the distal array remains against its stop. In this fashion, the distal spring and its mechanical stop cooperate with the proximal spring force to stabilize the array deployment during catheter deflection. FIG. 10A and FIG. 10B show an alternative embodiment for deploying the array of the catheter. In this embodiment a screw 153 is positioned in the distal segment of the catheter. This screw 153 is rotated by a rotatable member or shaft 161 driven by a knob located in the handle which is not illustrated in the figures. The rotatable member 161 is keyed to the distal array segment 36 with the construction in section 155. The construction provides the counter-force against which distal array segment 26 is deployed and retracted. This construction also isolates the screw 153 and prevents it from being influenced by tension in the rotatable member 161. A complimentary nut forms a pull member 159 is free to slide over the stationary screw. The pull member 159 has an end anchored in the distal tip of the array and the traction supplied by the screw 153 causes the pull member 159 to move retrograde deploying the splines 50 of the array as seen in FIG. 10B. This construction renders the deployment function independent of the articulation function of the catheter since the deployment function is unaffected by the tension on rotatable member 161. In addition, this embodiment permits the array to deploy to known continuous intermediate states or positions between the fully retracted and fully deployed states. These continuous intermediate positions are useful in mapping operations where it is desirable to introduce the catheter into structures smaller than its fully deployed diameter while maintaining accurate knowledge of electrode locations. Electrode locations are determined from the amount of deployment which can be derived from the number of rotations employed by the rotatable member during deployment.

What is claimed is:

1. A catheter comprising:
an elongate catheter body having a distal end and a proximal end;
a proximal handle segment having an articulation control and a deployment control, said proximal handle segment connected to said proximal end;
an intermediate segment connected to said handle segment;
a deflectable segment connected to said intermediate segment, said deflectable segment adapted to articulate in a plane through an angle in response to said articulation control;
a distal array segment connected to said deflectable segment, said distal array segment including a deployable electrode array that can move from a first retracted position to a second deployed position, the deployed position comprising a known, reproducible, and relatively stiff shape; said deployable electrode array formed from a flexible printed circuit slit to form splines and rolled about a major axis, the splines of the flexible printed circuit including first regions having a first stiffness and second regions that include one or more stiffener layers and have a second stiffness that is greater than the first stiffness, the first stiffness and the second stiffness at least partially determining the shape of the electrode array in the deployed position, said distal array segment has a non-uniform distribution of electrodes along at least some of the splines with the electrodes being distributed more densely in a distal tip area of the splines.

2. The catheter of claim 1 wherein:
each spline in said deployable electrode array has a non-uniform shape characteristic resulting in control of the shape of the electrode array in the deployed position.

3. The catheter of claim 1 wherein:
said deployable electrode array having bonding apertures at an end of the array adapted for encapsulation to form and retain a tubular shape.

4. The catheter of claim 1 wherein:
said deployable electrode array having bonding apertures at an end of the array adapted for encapsulation by a thermoplastic material to form and retain a tubular shape.

5. The catheter of claim 1 wherein:
the flexible printed circuit comprises:
an insulating layer;
a first metal layer supported by a first surface of the insulating layer and a second metal layer supported by a second surface of the insulating layer, the first and second metal layers comprising an electrode material selected from the group consisting of: gold, stainless steel, platinum, platinum-iridium, titanium nitride, platinum black and iridium-oxide;
an overcoat layer supported by the second metal layer configured to insulate the second metal layer;
a first stiffener layer supported by the overcoat layer; and
a second stiffener layer that is separate from the first stiffener layer and disposed on portions of the first stiffener layer to form the second regions that have the second stiffness that is greater than the first stiffness.

6. The catheter of claim 1 further comprising:
a fluid delivery lumen to flood the distal array segment with a fluid injected into the catheter.

7. The catheter of claim 1 further comprising:
a radio-opaque pattern applied to the distal array segment such that the pattern changes during deployment to provide a discernable radiographic image to confirm deployment.

8. A catheter comprising:
an elongate catheter body having a distal end and a proximal end;
a proximal handle segment having deployment control, said proximal handle segment connected to said proximal end;
a distal array segment that includes multiple splines about a major axis including an electrode array having a non-uniform distribution of electrodes along at least some of the splines with the electrodes being distributed more densely in a distal tip area of the splines, said distal array segment connected to said distal end;
said electrode array formed from a flexible printed circuit and comprising:
an insulating layer comprising a first side and a second side;
a first metallization layer coated with iridium oxide on the first side of the insulating layer, the first metallization layer configured to increase the surface area of the first metallization layer;
a second metallization layer on the second side of the insulating layer; and
an electrical connection between the first metallization layer and the second metallization layer; and
a radio-opaque pattern applied to the distal array segment such that the pattern changes during deployment to provide a discernable radiographic image to confirm deployment.

9. The catheter of claim 8, wherein the first metallization layer comprises a plurality of metal layers.

10. The catheter of claim 8, wherein the first metallization layer comprises:
a titanium layer supported by the insulating layer;
a gold layer supported by the titanium layer; and
the iridium-oxide coating supported by the gold layer.

11. The catheter of claim 8, wherein the first metallization layer comprises:
an interface layer supported by the insulating layer;
a conductive layer comprising a copper or gold layer supported by the insulating layer; and
the iridium-oxide coating supported by the conductive layer.

12. The catheter of claim 8, wherein the first metallization layer comprises:
a conductive layer comprising a copper or gold layer; and
the iridium-oxide coating supported by the conductive layer.

13. The catheter of claim 8, wherein the metallization layer comprises a plurality of metal layers.

14. The catheter of claim 8, wherein the electrical connection between the first metallization layer and the second metallization layer comprises a metallization layer in a via that extends through the first metallization layer, the insulating layer, and the second metallization layer.

15. The catheter of claim 8, wherein the radio-opaque pattern comprises one or more radio-opaque devices selected from the group consisting of marker bands, coiled wire, and radiopaque ink.

16. A catheter comprising:
- an elongate catheter body having a distal end and a proximal end;
- a proximal handle segment having an articulation control and a deployment control, said proximal handle segment connected to said proximal end;
- an intermediate segment connected to said handle segment;
- a deflectable segment connected to said intermediate segment, said deflectable segment adapted to articulate in a plane through an angle in response to said articulation control;
- a distal array segment connected to said deflectable segment, said distal array segment including a deployable electrode array that can move from a first retracted position to a second deployed position, the deployed position comprising a known, reproducible, and relatively stiff shape, wherein said deployable electrode array is formed from a flexible printed circuit comprising:
- an insulating layer;
- a first metal layer supported by a first surface of the insulating layer and a second metal layer supported by a second surface of the insulating layer, the first and second metal layers comprising an electrode material selected from the group consisting of: gold, stainless steel, platinum, platinum-iridium, titanium nitride, platinum black and iridium-oxide;
- an overcoat layer supported by the second metal layer configured to insulate the second metal layer;
- a first stiffener layer supported by the overcoat layer; and
- a second stiffener layer that is separate from the first stiffener layer and disposed on portions of the first stiffener layer to form second regions that have a second stiffness that is greater than a first stiffness of the first stiffener layer.

17. The catheter of claim 16 further comprising:
a fluid delivery lumen to flood the distal array segment with a fluid injected into the catheter.

18. The catheter of claim 16 further comprising:
a radio-opaque pattern applied to the distal array segment such that the pattern changes during deployment to provide a discernable radiographic image to confirm deployment.

19. The catheter of claim 16 wherein:
said distal array segment has a non-uniform distribution of electrodes in the array with the electrodes being distributed more densely in regions of the deployed array that are more likely to be positioned closely to an endocardium surface.

* * * * *